(12) United States Patent
Bradley (10) Patent No.: US 9,517,344 B1
(45) Date of Patent: Dec. 13, 2016

(54) SYSTEMS AND METHODS FOR SELECTING LOW-POWER, EFFECTIVE SIGNAL DELIVERY PARAMETERS FOR AN IMPLANTED PULSE GENERATOR

(71) Applicant: Nevro Corporation, Redwood City, CA (US)

(72) Inventor: Kerry Bradley, Glendale, CA (US)

(73) Assignee: Nevro Corporation, Redwood City, CA (US)

( * ) Notice: Subject to any disclaimer, the term of this patent is extended or adjusted under 35 U.S.C. 154(b) by 0 days.

(21) Appl. No.: 15/057,913

(22) Filed: Mar. 1, 2016

Related U.S. Application Data

(63) Continuation of application No. 14/657,971, filed on Mar. 13, 2015, now abandoned.

(51) Int. Cl.
*A61N 1/36* (2006.01)
*A61N 1/372* (2006.01)

(52) U.S. Cl.
CPC ....... *A61N 1/36071* (2013.01); *A61N 1/36132* (2013.01); *A61N 1/36171* (2013.01); *A61N 1/37247* (2013.01)

(58) Field of Classification Search
None
See application file for complete search history.

(56) References Cited

U.S. PATENT DOCUMENTS

| | | |
|---|---|---|
| 3,871,382 A | 3/1975 | Mann |
| 4,019,519 A | 4/1977 | Geerling |
| 4,071,032 A | 1/1978 | Schulman |
| 4,082,097 A | 4/1978 | Mann et al. |
| 4,197,850 A | 4/1980 | Schulman et al. |
| 4,210,151 A | 7/1980 | Keller, Jr. |
| 4,230,121 A | 10/1980 | Stanton |
| 4,257,429 A | 3/1981 | Dickhudt et al. |
| 4,340,063 A | 7/1982 | Maurer |

(Continued)

FOREIGN PATENT DOCUMENTS

| | | |
|---|---|---|
| EP | 1331965 A2 | 8/2003 |
| JP | 08503648 | 4/1996 |

(Continued)

OTHER PUBLICATIONS

North et al., "Spinal Cord Stimulation for Axial Low Back Pain," SPINE, vol. 30, No. 12, 2005, 7 pages.

(Continued)

*Primary Examiner* — Brian T Gedeon
*Assistant Examiner* — Ankit D Tejani
(74) *Attorney, Agent, or Firm* — Perkins Coie LLP (57) ABSTRACT

Systems and methods for selecting low-power, effective signal delivery parameters for an implanted pulse generator are disclosed. A representative system includes a signal generator and a computer-readable medium that, for first and second signals, increases and decreases an amplitude of the signal over multiple steps from a baseline amplitude at which the patient has a baseline response. At individual step increases and decreases, the system receives a pain score based on the patient's response. The instructions compare the pain scores for the two signals and determine one of the signals for additional therapy to the patient, based on the pain scores and an expected energy consumption of the signals.

23 Claims, 4 Drawing Sheets

(56) References Cited

U.S. PATENT DOCUMENTS

| | | |
|---|---|---|
| 4,441,498 A | 4/1984 | Nordling |
| 4,467,800 A | 8/1984 | Zytkovicz |
| 4,550,733 A | 11/1985 | Liss et al. |
| 4,559,948 A | 12/1985 | Liss et al. |
| 4,628,942 A | 12/1986 | Sweeney et al. |
| 4,632,117 A | 12/1986 | James |
| 4,649,936 A | 3/1987 | Ungar et al. |
| 4,890,616 A | 1/1990 | Pinckaers |
| 4,899,750 A | 2/1990 | Ekwall |
| 5,031,618 A | 7/1991 | Mullett |
| 5,063,929 A | 11/1991 | Bartelt et al. |
| 5,065,083 A | 11/1991 | Owens |
| 5,069,211 A | 12/1991 | Bartelt et al. |
| 5,143,081 A | 9/1992 | Young et al. |
| 5,144,946 A | 9/1992 | Weinberg et al. |
| 5,159,926 A | 11/1992 | Ljungstroem |
| 5,184,617 A | 2/1993 | Harris et al. |
| 5,222,494 A | 6/1993 | Baker, Jr. |
| 5,223,226 A | 6/1993 | Wittmer et al. |
| 5,279,292 A | 1/1994 | Baumann et al. |
| 5,335,657 A | 8/1994 | Terry, Jr. et al. |
| 5,342,409 A | 8/1994 | Mullett |
| 5,354,320 A | 10/1994 | Schaldach et al. |
| 5,423,329 A | 6/1995 | Ergas |
| 5,540,730 A | 7/1996 | Terry, Jr. et al. |
| 5,641,326 A | 6/1997 | Adams |
| 5,643,330 A | 7/1997 | Holsheimer et al. |
| 5,702,429 A | 12/1997 | King |
| 5,733,313 A | 3/1998 | Barreras, Sr. et al. |
| 5,769,877 A | 6/1998 | Barreras, Sr. |
| 5,782,884 A | 7/1998 | Stotts et al. |
| 5,807,397 A | 9/1998 | Barreras |
| 5,814,092 A | 9/1998 | King |
| 5,843,146 A | 12/1998 | Cross, Jr. |
| 5,891,179 A | 4/1999 | Er et al. |
| 5,913,882 A | 6/1999 | King |
| 5,916,237 A | 6/1999 | Schu |
| 5,928,272 A | 7/1999 | Adkins et al. |
| 5,938,690 A | 8/1999 | Law |
| 5,954,758 A | 9/1999 | Peckham et al. |
| 6,026,328 A | 2/2000 | Peckham et al. |
| 6,052,624 A | 4/2000 | Mann |
| 6,076,018 A | 6/2000 | Sturman et al. |
| 6,115,634 A | 9/2000 | Donders et al. |
| 6,155,267 A | 12/2000 | Nelson |
| 6,159,163 A | 12/2000 | Strauss et al. |
| 6,167,303 A | 12/2000 | Thompson |
| 6,185,452 B1 | 2/2001 | Schulman et al. |
| 6,185,454 B1 | 2/2001 | Thompson |
| 6,208,894 B1 | 3/2001 | Schulman et al. |
| 6,223,080 B1 | 4/2001 | Thompson |
| 6,236,888 B1 | 5/2001 | Thompson |
| 6,236,892 B1 | 5/2001 | Feler |
| 6,308,102 B1 | 10/2001 | Sieracki et al. |
| 6,324,426 B1 | 11/2001 | Thompson |
| 6,341,236 B1 | 1/2002 | Osorio et al. |
| 6,353,762 B1 | 3/2002 | Baudino et al. |
| 6,381,496 B1 | 4/2002 | Meadows et al. |
| 6,393,325 B1 | 5/2002 | Mann et al. |
| 6,393,328 B1 | 5/2002 | McGraw et al. |
| 6,434,425 B1 | 8/2002 | Thompson |
| 6,440,090 B1 | 8/2002 | Schallhorn |
| 6,453,198 B1 | 9/2002 | Torgerson et al. |
| 6,461,357 B1 | 10/2002 | Sharkey et al. |
| 6,496,729 B2 | 12/2002 | Thompson |
| 6,516,227 B1 | 2/2003 | Meadows et al. |
| 6,553,263 B1 | 4/2003 | Meadows et al. |
| 6,565,593 B2 | 5/2003 | Diana |
| 6,574,507 B1 | 6/2003 | Bonnet |
| 6,587,727 B2 | 7/2003 | Osorio et al. |
| 6,609,030 B1 | 8/2003 | Rezai et al. |
| 6,609,032 B1 | 8/2003 | Woods et al. |
| 6,622,048 B1 | 9/2003 | Mann |
| 6,650,943 B1 | 11/2003 | Whitehurst et al. |
| 6,659,968 B1 | 12/2003 | McClure |
| 6,671,556 B2 | 12/2003 | Osorio et al. |
| 6,712,772 B2 | 3/2004 | Cohen et al. |
| 6,740,072 B2 | 5/2004 | Starkweather et al. |
| 6,757,561 B2 | 6/2004 | Rubin et al. |
| 6,871,099 B1 | 3/2005 | Whitehurst et al. |
| 6,873,872 B2 | 3/2005 | Gluckman et al. |
| 6,895,280 B2 | 5/2005 | Meadows et al. |
| 6,909,917 B2 | 6/2005 | Woods et al. |
| 6,920,357 B2 | 7/2005 | Osorio et al. |
| 6,947,792 B2 | 9/2005 | Ben-Haim et al. |
| 6,950,707 B2 | 9/2005 | Whitehurst |
| 6,961,618 B2 | 11/2005 | Osorio et al. |
| 6,978,171 B2 | 12/2005 | Goetz et al. |
| 6,993,384 B2 | 1/2006 | Bradley et al. |
| 7,010,345 B2 | 3/2006 | Hill et al. |
| 7,020,523 B1 | 3/2006 | Lu et al. |
| 7,024,246 B2 | 4/2006 | Acosta et al. |
| 7,024,247 B2 | 4/2006 | Gliner et al. |
| 7,027,860 B2 | 4/2006 | Bruninga et al. |
| 7,050,856 B2 | 5/2006 | Stypulkowski |
| 7,054,689 B2 | 5/2006 | Whitehurst et al. |
| 7,110,821 B1 | 9/2006 | Ross |
| 7,120,499 B2 | 10/2006 | Thrope et al. |
| 7,123,967 B2 | 10/2006 | Weinberg |
| 7,127,288 B2 | 10/2006 | Sturman et al. |
| 7,127,296 B2 | 10/2006 | Bradley |
| 7,142,923 B2 | 11/2006 | North et al. |
| 7,167,756 B1 | 1/2007 | Torgerson et al. |
| 7,174,215 B2 | 2/2007 | Bradley |
| 7,177,703 B2 | 2/2007 | Boveja et al. |
| 7,184,836 B1 | 2/2007 | Meadows et al. |
| 7,184,837 B2 | 2/2007 | Goetz |
| 7,191,012 B2 | 3/2007 | Boveja et al. |
| 7,206,632 B2 | 4/2007 | King |
| 7,209,792 B1 | 4/2007 | Parramon et al. |
| 7,239,920 B1 | 7/2007 | Thacker et al. |
| 7,239,926 B2 | 7/2007 | Goetz |
| 7,242,984 B2 | 7/2007 | DiLorenzo |
| 7,252,090 B2 | 8/2007 | Goetz |
| 7,254,449 B2 | 8/2007 | Karunasiri |
| 7,263,402 B2 | 8/2007 | Thacker et al. |
| 7,266,412 B2 | 9/2007 | Stypulkowski |
| 7,286,878 B2 | 10/2007 | Stypulkowski |
| 7,289,851 B2 | 10/2007 | Gunderson et al. |
| 7,295,876 B1 | 11/2007 | Erickson |
| 7,317,948 B1 | 1/2008 | King et al. |
| 7,330,762 B2 | 2/2008 | Boveja et al. |
| 7,337,010 B2 | 2/2008 | Howard et al. |
| 7,343,200 B2 | 3/2008 | Litvak et al. |
| 7,349,739 B2 | 3/2008 | Harry et al. |
| 7,386,348 B2 | 6/2008 | North et al. |
| 7,403,821 B2 | 7/2008 | Haugland et al. |
| 7,406,351 B2 | 7/2008 | Wesselink |
| 7,437,193 B2 | 10/2008 | Parramon et al. |
| 7,444,181 B2 | 10/2008 | Shi et al. |
| 7,447,545 B2 | 11/2008 | Heruth et al. |
| 7,450,992 B1 | 11/2008 | Cameron |
| 7,463,927 B1 | 12/2008 | Chaouat |
| 7,483,747 B2 | 1/2009 | Gliner et al. |
| 7,489,968 B1 | 2/2009 | Alexander et al. |
| 7,489,970 B2 | 2/2009 | Lee et al. |
| 7,496,404 B2 | 2/2009 | Meadows et al. |
| 7,555,346 B1 | 6/2009 | Woods et al. |
| 7,571,001 B2 | 8/2009 | Thacker et al. |
| 7,571,002 B2 | 8/2009 | Thrope et al. |
| 7,603,175 B2 | 10/2009 | Voelkel |
| 7,606,622 B2 | 10/2009 | Reeve |
| 7,616,990 B2 | 11/2009 | Chavan et al. |
| 7,617,002 B2 | 11/2009 | Goetz |
| 7,620,454 B2 | 11/2009 | Dinsmoor et al. |
| 7,634,315 B2 | 12/2009 | Cholette |
| 7,636,602 B2 | 12/2009 | Baru Fassio et al. |
| 7,641,992 B2 | 1/2010 | Howard et al. |
| 7,647,101 B2 | 1/2010 | Libbus et al. |
| 7,650,191 B1 | 1/2010 | Lim et al. |
| 7,657,317 B2 | 2/2010 | Thacker et al. |
| 7,660,628 B2 | 2/2010 | Libbus et al. |
| 7,682,745 B2 | 3/2010 | Howard et al. |
| 7,697,984 B2 | 4/2010 | Hill et al. |

(56) References Cited

U.S. PATENT DOCUMENTS

| | | |
|---|---|---|
| 7,706,889 B2 | 4/2010 | Gerber et al. |
| 7,747,330 B2 | 6/2010 | Nolan et al. |
| 7,751,900 B2 | 7/2010 | Voelkel |
| 7,769,442 B2 | 8/2010 | Shafer |
| 7,769,462 B2 | 8/2010 | Meadows et al. |
| 7,783,349 B2 | 8/2010 | Libbus et al. |
| 7,799,021 B2 | 9/2010 | Leung et al. |
| 7,801,601 B2 | 9/2010 | Maschino et al. |
| 7,801,615 B2 | 9/2010 | Meadows et al. |
| 7,801,619 B2 | 9/2010 | Gerber et al. |
| 7,801,621 B1 | 9/2010 | Thacker et al. |
| 7,818,068 B2 | 10/2010 | Meadows et al. |
| 7,819,909 B2 | 10/2010 | Goetz et al. |
| 7,831,305 B2 | 11/2010 | Gliner |
| 7,831,307 B1 | 11/2010 | Moffitt |
| 7,853,322 B2 | 12/2010 | Bourget et al. |
| 7,853,323 B2 | 12/2010 | Goetz |
| 7,865,245 B2 | 1/2011 | Torgerson et al. |
| 7,872,884 B2 | 1/2011 | Parramon et al. |
| 7,873,418 B2 | 1/2011 | Stypulkowski |
| 7,879,495 B2 | 2/2011 | Howard et al. |
| 7,881,805 B2 | 2/2011 | Bradley et al. |
| 7,916,013 B2 | 3/2011 | Stevenson |
| 7,945,330 B2 | 5/2011 | Gliner et al. |
| 7,957,797 B2 | 6/2011 | Bourget et al. |
| 7,957,809 B2 | 6/2011 | Bourget et al. |
| 7,957,814 B2 | 6/2011 | Goetz et al. |
| 7,966,073 B2 | 6/2011 | Pless et al. |
| 7,967,839 B2 | 6/2011 | Flock et al. |
| 8,016,776 B2 | 9/2011 | Bourget et al. |
| 8,095,220 B2 | 1/2012 | Lee et al. |
| 8,116,878 B1 | 2/2012 | Palmer |
| 8,121,703 B1 | 2/2012 | Palmer |
| 8,128,600 B2 | 3/2012 | Gill |
| 8,175,719 B2 | 5/2012 | Shi et al. |
| 8,311,639 B2 | 11/2012 | Parker et al. |
| 8,355,797 B2 | 1/2013 | Caparso et al. |
| 8,457,759 B2 | 6/2013 | Parker et al. |
| 8,498,710 B2 | 7/2013 | Walker et al. |
| 8,626,312 B2 | 1/2014 | King et al. |
| 8,712,533 B2 | 4/2014 | Alataris et al. |
| 8,712,535 B2 | 4/2014 | Walker et al. |
| 2002/0068930 A1 | 6/2002 | Tasto et al. |
| 2002/0107554 A1 | 8/2002 | Biggs et al. |
| 2002/0165586 A1 | 11/2002 | Hill et al. |
| 2002/0193844 A1 | 12/2002 | Michelson et al. |
| 2003/0004549 A1 | 1/2003 | Hill et al. |
| 2003/0093134 A1 | 5/2003 | Bradley |
| 2003/0100931 A1 | 5/2003 | Mullett |
| 2003/0114899 A1 | 6/2003 | Woods et al. |
| 2003/0135241 A1 | 7/2003 | Leonard et al. |
| 2003/0135248 A1* | 7/2003 | Stypulkowski .... A61N 1/36071 607/73 |
| 2003/0153959 A1 | 8/2003 | Thacker et al. |
| 2003/0191504 A1 | 10/2003 | Meadows et al. |
| 2003/0195581 A1 | 10/2003 | Meadows et al. |
| 2003/0195582 A1 | 10/2003 | Mann |
| 2003/0204222 A1 | 10/2003 | Leinders et al. |
| 2003/0208244 A1 | 11/2003 | Stein et al. |
| 2003/0212445 A1 | 11/2003 | Weinberg |
| 2004/0015188 A1 | 1/2004 | Coulter |
| 2004/0015202 A1 | 1/2004 | Chandler et al. |
| 2004/0034394 A1 | 2/2004 | Woods et al. |
| 2004/0093093 A1 | 5/2004 | Andrews |
| 2004/0116978 A1 | 6/2004 | Bradley |
| 2004/0138516 A1 | 7/2004 | Osorio et al. |
| 2004/0167584 A1 | 8/2004 | Carroll et al. |
| 2004/0215286 A1 | 10/2004 | Stypulkowski |
| 2004/0215287 A1 | 10/2004 | Swoyer et al. |
| 2005/0033381 A1 | 2/2005 | Carter et al. |
| 2005/0060001 A1 | 3/2005 | Singhal et al. |
| 2005/0060007 A1 | 3/2005 | Goetz |
| 2005/0143787 A1 | 6/2005 | Boveja et al. |
| 2005/0149146 A1 | 7/2005 | Boveja et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0187590 A1 | 8/2005 | Boveja et al. |
| 2005/0197678 A1 | 9/2005 | Boveja et al. |
| 2005/0203584 A1 | 9/2005 | Twetan et al. |
| 2005/0209655 A1 | 9/2005 | Bradley et al. |
| 2005/0216070 A1 | 9/2005 | Boveja et al. |
| 2005/0245987 A1 | 11/2005 | Woods et al. |
| 2006/0111754 A1 | 5/2006 | Rezai et al. |
| 2006/0116742 A1 | 6/2006 | De Ridder |
| 2006/0135998 A1 | 6/2006 | Libbus et al. |
| 2006/0161236 A1 | 7/2006 | King |
| 2006/0190048 A1 | 8/2006 | Gerber |
| 2006/0195159 A1 | 8/2006 | Bradley et al. |
| 2006/0235472 A1 | 10/2006 | Goetz et al. |
| 2006/0247732 A1 | 11/2006 | Wesselink |
| 2006/0253174 A1 | 11/2006 | King |
| 2006/0253182 A1 | 11/2006 | King |
| 2006/0259079 A1 | 11/2006 | King |
| 2006/0259099 A1 | 11/2006 | Goetz et al. |
| 2006/0293720 A1 | 12/2006 | DiLorenzo |
| 2007/0039625 A1 | 2/2007 | Heruth et al. |
| 2007/0060955 A1 | 3/2007 | Strother et al. |
| 2007/0060968 A1 | 3/2007 | Strother et al. |
| 2007/0060980 A1 | 3/2007 | Strother et al. |
| 2007/0073357 A1 | 3/2007 | Rooney et al. |
| 2007/0093875 A1 | 4/2007 | Chavan et al. |
| 2007/0100378 A1 | 5/2007 | Maschino |
| 2007/0129774 A1 | 6/2007 | Bourget et al. |
| 2007/0150029 A1 | 6/2007 | Bourget et al. |
| 2007/0156207 A1 | 7/2007 | Kothandaraman et al. |
| 2007/0179559 A1 | 8/2007 | Giftakis et al. |
| 2007/0179579 A1 | 8/2007 | Feler et al. |
| 2007/0208394 A1 | 9/2007 | King et al. |
| 2007/0213773 A1 | 9/2007 | Hill et al. |
| 2007/0213789 A1 | 9/2007 | Nolan et al. |
| 2007/0233192 A1 | 10/2007 | Craig |
| 2007/0245318 A1 | 10/2007 | Goetz et al. |
| 2007/0249968 A1 | 10/2007 | Miesel et al. |
| 2007/0255118 A1 | 11/2007 | Miesel et al. |
| 2007/0265679 A1 | 11/2007 | Bradley et al. |
| 2007/0265681 A1 | 11/2007 | Gerber et al. |
| 2007/0270916 A1 | 11/2007 | Fischell et al. |
| 2007/0270921 A1 | 11/2007 | Strother et al. |
| 2007/0276450 A1 | 11/2007 | Meadows et al. |
| 2007/0276453 A1 | 11/2007 | Hill et al. |
| 2008/0015657 A1 | 1/2008 | Haefner |
| 2008/0039904 A1 | 2/2008 | Bulkes et al. |
| 2008/0046036 A1 | 2/2008 | King et al. |
| 2008/0046052 A1 | 2/2008 | Werder et al. |
| 2008/0051839 A1 | 2/2008 | Libbus et al. |
| 2008/0058901 A1 | 3/2008 | Ternes et al. |
| 2008/0064980 A1 | 3/2008 | Lee et al. |
| 2008/0065182 A1 | 3/2008 | Strother et al. |
| 2008/0071325 A1 | 3/2008 | Bradley |
| 2008/0077184 A1 | 3/2008 | Denker et al. |
| 2008/0097554 A1 | 4/2008 | Payne et al. |
| 2008/0103570 A1 | 5/2008 | Gerber |
| 2008/0109050 A1 | 5/2008 | John |
| 2008/0125833 A1 | 5/2008 | Bradley et al. |
| 2008/0132926 A1 | 6/2008 | Eichmann et al. |
| 2008/0140150 A1 | 6/2008 | Zhou et al. |
| 2008/0154340 A1 | 6/2008 | Goetz et al. |
| 2008/0156333 A1 | 7/2008 | Galpern et al. |
| 2008/0183256 A1 | 7/2008 | Keacher |
| 2008/0188909 A1 | 8/2008 | Bradley |
| 2008/0215118 A1 | 9/2008 | Goetz et al. |
| 2008/0215119 A1 | 9/2008 | Woods et al. |
| 2008/0216846 A1 | 9/2008 | Levin |
| 2008/0234791 A1 | 9/2008 | Arle et al. |
| 2008/0243196 A1 | 10/2008 | Libbus et al. |
| 2008/0255631 A1 | 10/2008 | Sjostedt et al. |
| 2008/0262563 A1 | 10/2008 | Sjostedt |
| 2008/0269843 A1 | 10/2008 | Gerber et al. |
| 2008/0275529 A1 | 11/2008 | North et al. |
| 2008/0281381 A1 | 11/2008 | Gerber et al. |
| 2008/0319511 A1 | 12/2008 | Pless |
| 2009/0005833 A1 | 1/2009 | Cameron et al. |
| 2009/0017700 A1 | 1/2009 | Zart et al. |

(56) References Cited

U.S. PATENT DOCUMENTS

| | | |
|---|---|---|
| 2009/0018600 A1 | 1/2009 | Deininger et al. |
| 2009/0018617 A1 | 1/2009 | Skelton et al. |
| 2009/0030476 A1 | 1/2009 | Hargrove |
| 2009/0054946 A1 | 2/2009 | Sommer et al. |
| 2009/0112281 A1 | 4/2009 | Miyazawa et al. |
| 2009/0112282 A1 | 4/2009 | Kast et al. |
| 2009/0125079 A1 | 5/2009 | Armstrong et al. |
| 2009/0132010 A1 | 5/2009 | Kronberg |
| 2009/0157138 A1 | 6/2009 | Errico et al. |
| 2009/0157142 A1 | 6/2009 | Cauller |
| 2009/0204119 A1 | 8/2009 | Bleich et al. |
| 2009/0204173 A1 | 8/2009 | Fang et al. |
| 2009/0210029 A1 | 8/2009 | Tsui |
| 2009/0248094 A1 | 10/2009 | McDonald |
| 2009/0248118 A1 | 10/2009 | Bradley et al. |
| 2009/0264956 A1 | 10/2009 | Rise et al. |
| 2009/0264957 A1 | 10/2009 | Giftakis et al. |
| 2009/0270948 A1 | 10/2009 | Nghiem et al. |
| 2009/0281594 A1 | 11/2009 | King et al. |
| 2009/0281595 A1 | 11/2009 | King et al. |
| 2009/0281596 A1 | 11/2009 | King et al. |
| 2009/0281599 A1 | 11/2009 | Thacker et al. |
| 2009/0306740 A1 | 12/2009 | Heruth et al. |
| 2009/0306746 A1 | 12/2009 | Blischak |
| 2009/0326608 A1 | 12/2009 | Huynh et al. |
| 2010/0004654 A1 | 1/2010 | Schmitz et al. |
| 2010/0010566 A1 | 1/2010 | Thacker et al. |
| 2010/0010567 A1 | 1/2010 | Deem et al. |
| 2010/0038132 A1 | 2/2010 | Kinney et al. |
| 2010/0049275 A1 | 2/2010 | Chavan et al. |
| 2010/0049280 A1 | 2/2010 | Goetz |
| 2010/0069993 A1 | 3/2010 | Greenspan |
| 2010/0094115 A1 | 4/2010 | Pond, Jr. et al. |
| 2010/0094231 A1 | 4/2010 | Bleich et al. |
| 2010/0106223 A1 | 4/2010 | Grevious et al. |
| 2010/0121408 A1 | 5/2010 | Imran et al. |
| 2010/0125314 A1 | 5/2010 | Bradley et al. |
| 2010/0131034 A1 | 5/2010 | Gliner et al. |
| 2010/0137943 A1 | 6/2010 | Zhu |
| 2010/0137944 A1 | 6/2010 | Zhu |
| 2010/0144281 A1 | 6/2010 | Kim et al. |
| 2010/0144283 A1 | 6/2010 | Curcio et al. |
| 2010/0168818 A1 | 7/2010 | Barror et al. |
| 2010/0185256 A1 | 7/2010 | Hulvershorn |
| 2010/0228325 A1 | 9/2010 | Moffitt et al. |
| 2010/0233896 A1 | 9/2010 | Dilmaghanian |
| 2010/0234912 A1 | 9/2010 | Ternes et al. |
| 2010/0274312 A1 | 10/2010 | Alataris et al. |
| 2010/0274314 A1 | 10/2010 | Alataris et al. |
| 2010/0274317 A1 | 10/2010 | Parker et al. |
| 2010/0274320 A1 | 10/2010 | Torgerson |
| 2010/0274336 A1 | 10/2010 | Nguyen-Stella et al. |
| 2010/0305631 A1 | 12/2010 | Bradley et al. |
| 2010/0305660 A1 | 12/2010 | Hegi et al. |
| 2010/0312319 A1 | 12/2010 | Barker |
| 2010/0324570 A1 | 12/2010 | Rooney et al. |
| 2011/0009927 A1 | 1/2011 | Parker et al. |
| 2011/0022141 A1 | 1/2011 | Chen et al. |
| 2011/0029040 A1 | 2/2011 | Walker et al. |
| 2011/0040348 A1 | 2/2011 | Wacnik et al. |
| 2011/0040351 A1 | 2/2011 | Butson et al. |
| 2011/0046697 A1 | 2/2011 | Gerber et al. |
| 2011/0054565 A1 | 3/2011 | Wacnik et al. |
| 2011/0054583 A1 | 3/2011 | Litt et al. |
| 2011/0071593 A1 | 3/2011 | Parker et al. |
| 2011/0087309 A1 | 4/2011 | Stypulkowski |
| 2011/0093051 A1 | 4/2011 | Davis et al. |
| 2011/0112601 A1 | 5/2011 | Meadows et al. |
| 2011/0112609 A1 | 5/2011 | Peterson |
| 2011/0118661 A1 | 5/2011 | Pless et al. |
| 2011/0144468 A1 | 6/2011 | Boggs et al. |
| 2011/0184488 A1 | 7/2011 | De Ridder |
| 2011/0224710 A1 | 9/2011 | Bleich |
| 2012/0083857 A1 | 4/2012 | Bradley et al. |
| 2012/0116476 A1 | 5/2012 | Kothandaraman |
| 2012/0130448 A1 | 5/2012 | Woods et al. |
| 2012/0172946 A1 | 7/2012 | Alataris et al. |
| 2012/0253422 A1 | 10/2012 | Thacker et al. |
| 2012/0265268 A1 | 10/2012 | Blum et al. |
| 2012/0265271 A1 | 10/2012 | Goetz |
| 2012/0315798 A1 | 12/2012 | Poon et al. |
| 2013/0023950 A1 | 1/2013 | Gauthier |
| 2013/0060302 A1 | 3/2013 | Polefko et al. |
| 2013/0066399 A1 | 3/2013 | Min |
| 2013/0066411 A1 | 3/2013 | Thacker et al. |
| 2013/0261694 A1 | 10/2013 | Caparso et al. |
| 2013/0310892 A1 | 11/2013 | Parker et al. |
| 2014/0081349 A1 | 3/2014 | Lee et al. |
| 2014/0330338 A1 | 11/2014 | Walker et al. |
| 2015/0217113 A1 | 8/2015 | Walker et al. |

FOREIGN PATENT DOCUMENTS

| | | |
|---|---|---|
| JP | 20020527159 | 8/2002 |
| JP | 2006502811 A | 1/2006 |
| JP | 2006212458 A | 8/2006 |
| JP | 2008526299 A | 7/2008 |
| JP | 2008534168 A | 8/2008 |
| JP | 2009519771 A | 5/2009 |
| WO | WO-0245791 A2 | 6/2002 |
| WO | WO-02096512 A1 | 12/2002 |
| WO | WO-2004098698 | 11/2004 |
| WO | WO-2006119046 A1 | 11/2006 |
| WO | WO-2007149018 A1 | 12/2007 |
| WO | WO-2008142402 A1 | 11/2008 |
| WO | WO-2008157182 A1 | 12/2008 |

OTHER PUBLICATIONS

North et al., "Spinal Cord Stimulation for Chronic, Intractable Pain: Experience over Two Decades," Neurosurgery, vol. 32, No. 2, Mar. 1993, 12 pages.

Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.

Walsh, Fergus, "Hope over pain relief implant which uses Wii technology," BBC New Health, http://www.bbc.co.uk/news/10509063, accessed Jul. 14, 2010, 3 pages.

Keuchmann C et al., "853 Could Automatic Position Adaptive Stimulation be Useful in Spinal Cord Stimulation," Abstract, Medtronic, Inc., undated, 1 page.

Hayt et al., "Engine Circuit Analysis," McGraw-Hill Book Company, Fourth Edition, 1986, 18 pages.

* cited by examiner

FIG. 3

SYSTEMS AND METHODS FOR SELECTING LOW-POWER, EFFECTIVE SIGNAL DELIVERY PARAMETERS FOR AN IMPLANTED PULSE GENERATOR

CROSS REFERENCE TO RELATED APPLICATION

The present application is a continuation of U.S. patent application Ser. No. 14/657,971, filed Mar. 13, 2015.

TECHNICAL FIELD

The present disclosure is directed to systems and methods for selecting low-power, effective signal delivery parameters for an implanted pulse generator. In particular applications, the techniques disclosed herein are applied in the context of delivering high-frequency, paresthesia-free therapy signals.

BACKGROUND

Neurological stimulators have been developed to treat pain, movement disorders, functional disorders, spasticity, cancer, cardiac disorders, and various other medical conditions. Implantable neurological stimulation systems generally have an implantable signal generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings (i.e., contacts) spaced apart from each other at the distal end of the lead body. The conductive rings operate as individual electrodes and, in many cases, the SCS leads are implanted percutaneously through a needle inserted into the epidural space, with or without the assistance of a stylet.

Once implanted, the signal generator applies electrical pulses to the electrodes, which in turn modify the function of the patient's nervous system, such as by altering the patient's responsiveness to sensory stimuli and/or altering the patient's motor-circuit output. In SCS therapy for the treatment of pain, the signal generator applies electrical pulses to the spinal cord via the electrodes. In conventional SCS therapy, electrical pulses are used to generate sensations (known as paresthesia) that mask or otherwise alter the patient's sensation of pain. For example, in many cases, patients report paresthesia as a tingling sensation that is perceived as less uncomfortable than the underlying pain sensation.

In contrast to traditional or conventional (i.e., paresthesia-based) SCS, a form of paresthesia-free SCS has been developed that uses therapy signal parameters that treat the patient's sensation of pain without generating paresthesia or otherwise using paresthesia to mask the patient's sensation of pain. One of several advantages of paresthesia-free SCS therapy systems is that they eliminate the need for uncomfortable paresthesias, which many patients find objectionable. However, a challenge with paresthesia-free SCS therapy systems is that the signal may be delivered at frequencies, amplitudes, and/or pulse widths that use more power than conventional SCS systems. As a result, there is a need to develop optimized systems and methods for effectively delivering therapy while efficiently using power resources.

DETAILED DESCRIPTION

General aspects of the environments in which the disclosed technology operates are described below under Heading 1.0 ("Overview") with reference to FIGS. 1A and 1B. Particular embodiments of the technology are described further under Heading 2.0 ("Representative Embodiments") with reference to FIGS. 2 and 3. Additional embodiments are described under Heading 3.0 ("Additional Embodiments").

1.0 Overview

One example of a paresthesia-free SCS therapy system is a "high frequency" SCS system. High frequency SCS systems can inhibit, reduce, and/or eliminate pain via waveforms with high frequency elements or components (e.g., portions having high fundamental frequencies), generally with reduced or eliminated side effects. Such side effects can include unwanted paresthesia, unwanted motor stimulation or blocking, unwanted pain or discomfort, and/or interference with sensory functions other than the targeted pain. In a representative embodiment, a patient may receive high frequency therapeutic signals with at least a portion of the therapy signal at a frequency of from about 1.5 kHz to about 100 kHz, or from about 1.5 kHz to about 50 kHz, or from about 3 kHz to about 20 kHz, or from about 5 kHz to about 15 kHz, or at frequencies of about 8 kHz, 9 kHz, or 10 kHz. These frequencies are significantly higher than the frequencies associated with conventional "low frequency" SCS, which are generally below 1,200 Hz, and more commonly below 100 Hz. Accordingly, modulation at these and other representative frequencies (e.g., from about 1.5 kHz to about 100 kHz) is occasionally referred to herein as "high frequency stimulation," "high frequency SCS," and/or "high frequency modulation." Further examples of paresthesia-free SCS systems are described in U.S. Patent Publication Nos. 2009/0204173 and 2010/0274314, the respective disclosures of which are herein incorporated by reference in their entireties.

Figure 1A:
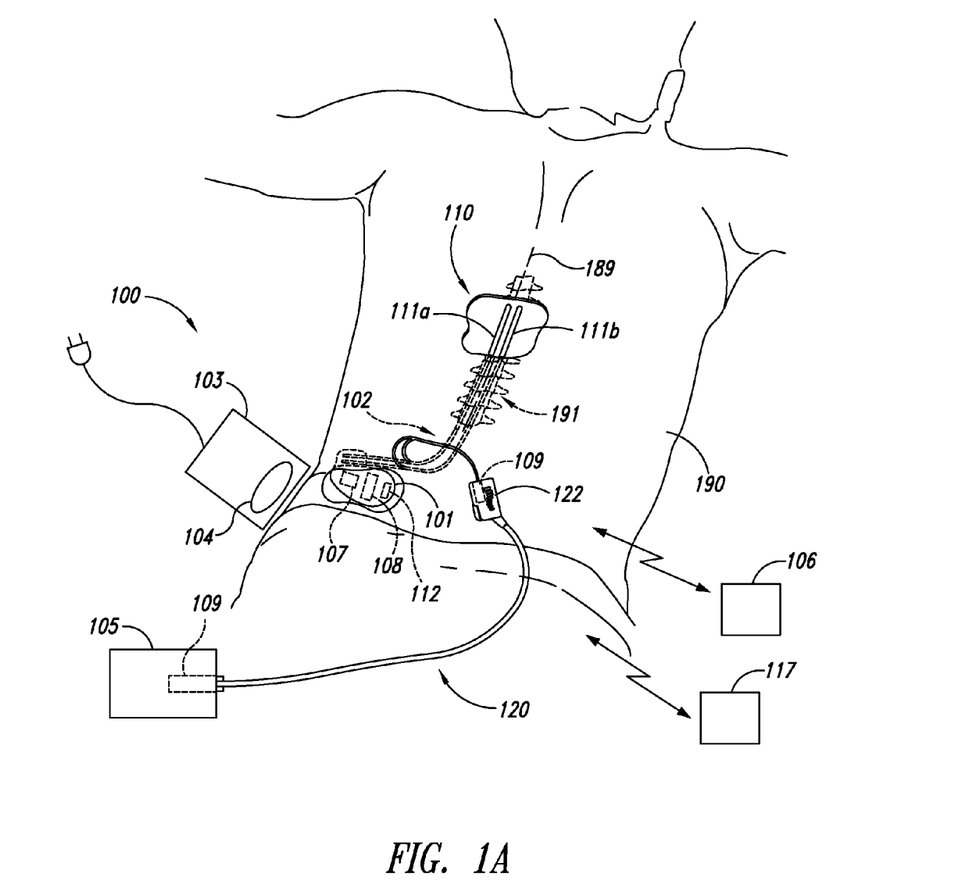
FIG. 1A is a partially schematic illustration of an implantable spinal cord modulation system positioned at the spine to deliver therapeutic signals in accordance with several embodiments in the present technology.

FIG. 1A schematically illustrates a representative patient therapy system 100 for providing relief from chronic pain and/or other conditions, arranged relative to the general anatomy of a patient's spinal column 191. The system 100 can include a signal generator 101 (e.g., an implanted or implantable pulse generator or IPG), which may be implanted subcutaneously within a patient 190 and coupled to one or more signal delivery elements or devices 110. The signal delivery elements or devices 110 may be implanted within the patient 190, typically at or near the patient's spinal cord midline 189. The signal delivery elements 110 carry features for delivering therapy to the patient 190 after implantation. As shown, the signal generator 101 can be implanted within the patient. In such an embodiment, the signal generator 101 can be connected directly to the signal delivery devices 110, or it can be coupled to the signal delivery devices 110 via a signal link or lead extension 102. In an embodiment wherein the signal generator is external to the patient, the signal generator can deliver a signal to the signal delivery device 110 via a wireless link, such as RF communication. In a further representative embodiment, the signal delivery devices 110 can include one or more elongated lead(s) or lead body or bodies 111 (identified individually as a first lead 111a and a second lead 111b). As used herein, the terms signal delivery device, lead, and/or lead body include any of a number of suitable substrates and/or support members that carry electrodes/devices for providing therapy signals to the patient 190. For example, the lead or leads 111 can include one or more electrodes or electrical contacts that direct electrical signals into the patient's tissue, e.g., to provide for therapeutic relief. In other embodiments, the signal delivery elements 110 can include structures other than a lead body (e.g., a paddle) that also direct electrical signals and/or other types of signals to the patient 190.

In a representative embodiment, one signal delivery device may be implanted on one side of the spinal cord midline 189, and a second signal delivery device may be implanted on the other side of the spinal cord midline 189. For example, the first and second leads 111a, 111b shown in FIG. 1A may be positioned just off the spinal cord midline 189 (e.g., about 1 mm offset) in opposing lateral directions so that the two leads 111a, 111b are spaced apart from each other by about 2 mm. In particular embodiments, the leads 111 may be implanted at a vertebral level ranging from, for example, about T8 to about T12. In other embodiments, one or more signal delivery devices can be implanted at other vertebral levels, e.g., as disclosed in U.S. Patent Application Publication No. 2013/0066411, which is incorporated herein by reference in its entirety.

The signal generator 101 can transmit signals (e.g., electrical signals) to the signal delivery elements 110 that up-regulate (e.g., excite) and/or down-regulate (e.g., block or suppress) target nerves. As used herein, and unless otherwise noted, the terms "modulate," "modulation," "stimulate," and "stimulation" refer generally to signals that have either type of the foregoing effects on the target nerves. The signal generator 101 can include a machine-readable (e.g., computer-readable) or controller-readable medium containing instructions for generating and transmitting suitable therapy signals. The signal generator 101 and/or other elements of the system 100 can include one or more processor(s) 107, memory unit(s) 108, and/or input/output device(s) 112. Accordingly, the process of providing modulation signals, providing guidance information for positioning the signal delivery devices 110, establishing battery charging and/or discharging parameters, establishing signal delivery parameters, and/or executing other associated functions can be performed by computer-executable instructions contained by, on or in computer-readable media located at the pulse generator 101 and/or other system components. Further, the pulse generator 101 and/or other system components may include dedicated hardware, firmware, and/or software for executing computer-executable instructions that, when executed, perform any one or more methods, processes, and/or sub-processes described herein; e.g., the methods, processes, and/or sub-processes described with reference to FIGS. 2-3 below. The dedicated hardware, firmware, and/or software also serve as "means for" performing the methods, processes, and/or sub-processes described herein. The signal generator 101 can also include multiple portions, elements, and/or subsystems (e.g., for directing signals in accordance with multiple signal delivery parameters), carried in a single housing, as shown in FIG. 1A, or in multiple housings.

The signal generator 101 can also receive and respond to an input signal received from one or more sources. The input signals can direct or influence the manner in which the therapy, charging, parameter selection and/or other process instructions are selected, executed, updated, and/or otherwise performed. The input signals can be received from one or more sensors (e.g., an input device 112 shown schematically in FIG. 1A for purposes of illustration) that are carried by the signal generator 101 and/or distributed outside the signal generator 101 (e.g., at other patient locations) while still communicating with the signal generator 101. The sensors and/or other input devices 112 can provide inputs that depend on or reflect patient state (e.g., patient position, patient posture, and/or patient activity level), and/or inputs that are patient-independent (e.g., time). Still further details are included in U.S. Pat. No. 8,355,797, incorporated herein by reference in its entirety.

In some embodiments, the signal generator 101 and/or signal delivery devices 110 can obtain power to generate the therapy signals from an external power source 103. In one embodiment, for example, the external power source 103 can by-pass an implanted signal generator and generate a therapy signal directly at the signal delivery devices 110 (or via signal relay components). The external power source 103 can transmit power to the implanted signal generator 101 and/or directly to the signal delivery devices 110 using electromagnetic induction (e.g., RF signals). For example, the external power source 103 can include an external coil 104 that communicates with a corresponding internal coil (not shown) within the implantable signal generator 101, signal delivery devices 110, and/or a power relay component (not shown). The external power source 103 can be portable for ease of use.

In another embodiment, the signal generator 101 can obtain the power to generate therapy signals from an internal power source, in addition to or in lieu of the external power source 103. For example, the implanted signal generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

During at least some procedures, an external stimulator or trial modulator 105 can be coupled to the signal delivery elements 110 during an initial procedure, prior to implanting the signal generator 101. For example, a practitioner (e.g., a physician and/or a company representative) can use the trial modulator 105 to vary the modulation parameters provided to the signal delivery elements 110 in real time, and select optimal or particularly efficacious parameters. These parameters can include the location from which the electrical signals are emitted, as well as the characteristics of the electrical signals provided to the signal delivery devices 110. In some embodiments, input is collected via the external stimulator or trial modulator and can be used by the clinician to help determine what parameters to vary. In a typical process, the practitioner uses a cable assembly 120 to temporarily connect the trial modulator 105 to the signal delivery device 110. The practitioner can test the efficacy of the signal delivery devices 110 in an initial position. The practitioner can then disconnect the cable assembly 120 (e.g., at a connector 122), reposition the signal delivery devices 110, and reapply the electrical signals. This process can be performed iteratively until the practitioner obtains the desired position for the signal delivery devices 110. Optionally, the practitioner may move the partially implanted signal delivery devices 110 without disconnecting the cable assembly 120. Furthermore, in some embodiments, the iterative process of repositioning the signal delivery devices 110 and/or varying the therapy parameters may not be performed.

The signal generator 101, the lead extension 102, the trial modulator 105 and/or the connector 122 can each include a receiving element 109. Accordingly, the receiving elements 109 can be patient implantable elements, or the receiving elements 109 can be integral with an external patient treatment element, device or component (e.g., the trial modulator 105 and/or the connector 122). The receiving elements 109 can be configured to facilitate a simple coupling and decoupling procedure between the signal delivery devices 110, the lead extension 102, the pulse generator 101, the trial modulator 105 and/or the connector 122. The receiving elements 109 can be at least generally similar in structure and function to those described in U.S. Patent Application Publication No. 2011/0071593, incorporated by reference herein in its entirety.

After the signal delivery elements 110 are implanted, the patient 190 can receive therapy via signals generated by the trial modulator 105, generally for a limited period of time. During this time, the patient wears the cable assembly 120 and the trial modulator 105 outside the body. Assuming the trial therapy is effective or shows the promise of being effective, the practitioner then replaces the trial modulator 105 with the implanted signal generator 101, and programs the signal generator 101 with therapy programs selected based on the experience gained during the trial period. Optionally, the practitioner can also replace the signal delivery elements 110. Once the implantable signal generator 101 has been positioned within the patient 190, the therapy programs provided by the signal generator 101 can still be updated remotely via a wireless physician's programmer (e.g., a physician's laptop, a physician's remote or remote device, etc.) 117 and/or a wireless patient programmer 106 (e.g., a patient's laptop, patient's remote or remote device, etc.). Generally, the patient 190 has control over fewer parameters than does the practitioner. For example, the capability of the patient programmer 106 may be limited to starting and/or stopping the signal generator 101, and/or adjusting the signal amplitude. The patient programmer 106 may be configured to accept pain relief input as well as other variables, such as medication use.

In any of the foregoing embodiments, the parameters in accordance with which the signal generator 101 provides signals can be adjusted during portions of the therapy regimen. For example, the frequency, amplitude, pulse width, and/or signal delivery location can be adjusted in accordance with a pre-set therapy program, patient and/or physician inputs, and/or in a random or pseudorandom manner. Such parameter variations can be used to address a number of potential clinical situations. Certain aspects of the foregoing systems and methods may be simplified or eliminated in particular embodiments of the present disclosure. Further aspects of these and other expected beneficial results are detailed in U.S. Patent Application Publication Nos. 2010/0274314; 2009/0204173; and 2013/0066411 (all previously incorporated by reference) and U.S. Patent Application Publication No. 2010/0274317, which is incorporated herein by reference in its entirety.

Figure 1B:
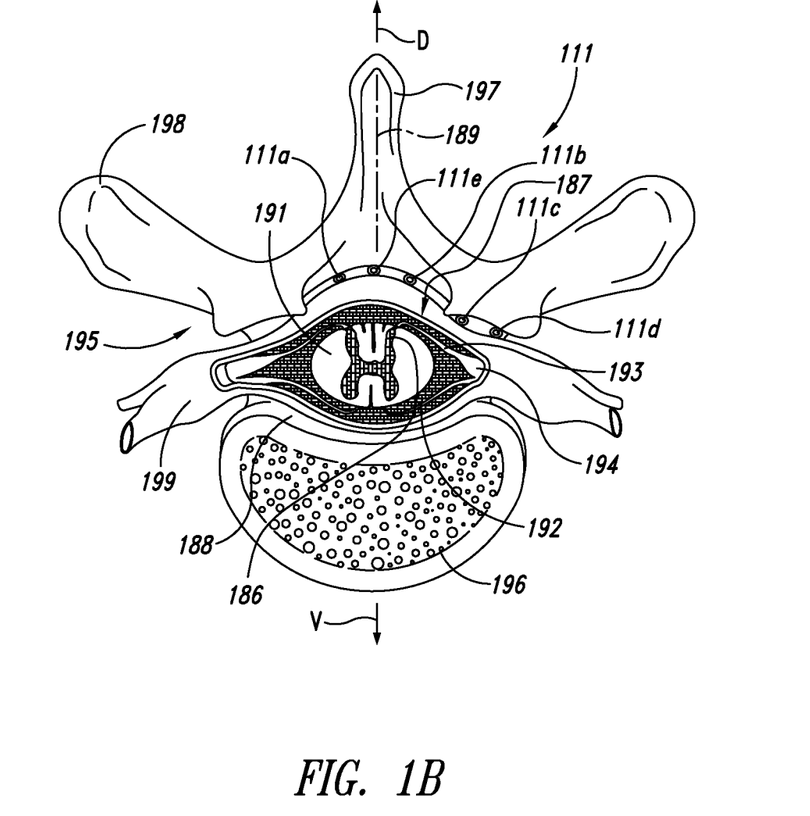
FIG. 1B is a partially schematic, cross-sectional illustration of a patient's spine, illustrating representative locations for implanted lead bodies in accordance with embodiments of the present technology.

FIG. 1B is a cross-sectional illustration of the spinal cord 191 and an adjacent vertebra 195 (based generally on information from Crossman and Neary, "Neuroanatomy," 1995 (published by Churchill Livingstone)), along with multiple leads 111 (shown as leads 111a-111e) implanted at representative locations. For purposes of illustration, multiple leads 111 are shown in FIG. 1B implanted in a single patient. In actual use, any given patient will likely receive fewer than all the leads 111 shown in FIG. 1B.

The spinal cord 191 is situated within a vertebral foramen 188, between a ventrally located ventral body 196 and a dorsally located transverse process 198 and spinous process 197. Arrows V and D identify the ventral and dorsal directions, respectively. The spinal cord 191 itself is located within the dura mater 199, which also surrounds portions of the nerves exiting the spinal cord 191, including the ventral roots 192, dorsal roots 193 and dorsal root ganglia 194. The dorsal roots 193 enter the spinal cord 191 at the dorsal root entry zone 187, and communicate with dorsal horn neurons located at the dorsal horn 186. In one embodiment, the first and second leads 111a, 111b are positioned just off the spinal cord midline 189 (e.g., about 1 mm. offset) in opposing lateral directions so that the two leads 111a, 111b are spaced apart from each other by about 2 mm, as discussed above. In other embodiments, a lead or pairs of leads can be positioned at other locations, e.g., toward the outer edge of the dorsal root entry zone 187 as shown by a third lead 111c, or at the dorsal root ganglia 194, as shown by a fourth lead 111d, or approximately at the spinal cord midline 189, as shown by a fifth lead 111e.

2.0 Representative Embodiments

Systems of the type described above with reference to FIGS. 1A-1B can include implanted pulse generators (IPGs) having rechargeable batteries or other rechargeable power sources that are periodically recharged with an external charger. In addition, such devices are configured to generate therapy signals, typically at higher frequencies than are used for conventional SCS, to produce pain relief without generating paresthesia in the patient. High frequency signals, however, may consume more energy than low frequency signals, e.g., for a given therapy, and may accordingly deplete the rechargeable power source more rapidly than conventional SCS therapy signals do. As a result, the patient may be required to recharge the implantable device more often than would be required for a conventional SCS device. Techniques in accordance with the present technology, described further below, can allow the system to automatically determine signal parameters that produce effective pain treatment with reduced (e.g., minimal) energy consumption.

In particular embodiments, embodiments of the therapy disclosed herein do not produce paresthesia or other undesirable side effects. This characteristic can significantly improve the degree to which the process for selecting the signal delivery parameters can be automated. In particular, with standard, conventional, low frequency SCS, the therapeutic efficacy (e.g., the degree of pain relief) typically increases with the amplitude of the signal. The power required to produce the signal also increases with amplitude. However, as the amplitude increases, other side effects, such as motor reflex and/or an overwhelming sensory intensity, overshadow the beneficial pain relief results. Accordingly, the approach for maximizing pain relief via conventional low frequency SCS therapy is typically to increase the amplitude of the signal until the patient can no longer tolerate the side effects. This can be a time-consuming operation, because the practitioner wishes to avoid overstimulating the patient. It also tends to result in a therapy signal that requires a large amount of power, due to the high amplitude. Still further, this process is typically not automated, so as to avoid inadvertently over-stimulating the patient as the amplitude is increased.

By contrast, it has been discovered that the therapeutic efficacy (e.g., level of pain relief) produced by a high frequency signal may begin to decrease at higher amplitudes, before other sensory or motor side-effects appear to limit further increases in amplitude. Because the therapeutic efficacy level is expected to decrease before the onset of unwanted motor or sensory effects, the presently disclosed systems and methods can automatically increment and/or decrement the stimulation amplitude, within pre-selected ranges (e.g., efficacy ranges), without triggering unwanted side effects. This technique can be used to identify an amplitude at one or more frequencies that both produces effective therapy, and does so at a relatively low energy consumption rate (e.g., power). Further details are described below.

Figure 2:
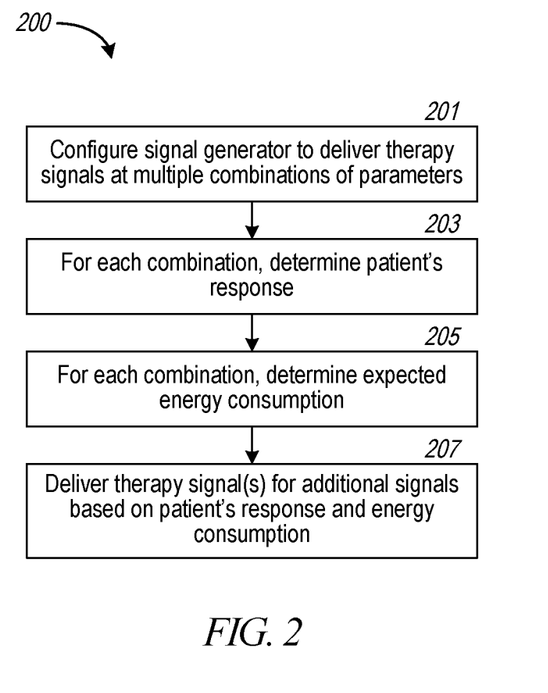
FIG. 2 is a flow diagram illustrating a process for selecting signal delivery parameters in accordance with an embodiment of the present technology.

FIG. 2 is a flow diagram illustrating a representative process 200 for selecting a therapy signal for delivery to a patient in accordance with an embodiment of the present technology. Process portion 201 includes configuring a signal generator to deliver therapy signals at multiple combinations of parameters. The parameters can include combinations of amplitudes and frequencies in particular embodiments. In other embodiments, the parameters can include other characteristics of the therapy signal, for example, the duty cycle, pulse width, and/or interpulse interval. In any of these embodiments, process portion 203 includes determining the patient's response to individual combinations (e.g., each combination) of applied signal parameters. The patient's response can be measured using any of a variety of suitable techniques that have been developed for identifying the patient's level of pain. Such techniques include using VAS scores, NRS scores, Likert satisfaction scales, Oswestry disability indices, among others. These techniques can be used to provide a patient-specific but quantifiable measure of the efficacy of the therapy, which is expected to change as the signal delivery parameters change. The foregoing techniques include feedback from the patient via deliberate patient participation (e.g., the patient consciously writing, describing or keying in a pain score). In other embodiments, the patient's response may be determined without this level of patient participation, e.g., by directly measuring patient physiological values that are correlated with the patient's pain level.

Process portion 205 includes determining the expected energy consumption for individual combinations (e.g., each combination) of signals applied to the patient. For example, process portion 205 can include integrating the area under a wave form graph of amplitude as a function of time. Accordingly, signals with high amplitudes and high frequencies consume more power than signals with low amplitudes and low frequencies. However, in particular embodiments, signals with high frequencies but low amplitudes can consume more power than signals with low frequencies and high amplitudes, and vice versa. The level of computation used to determine whether a particular combination of signal delivery parameters consumes more energy than another can vary in complexity, as will be described in further detail later.

Process portion 207 includes delivering one or more therapy signals for additional therapy based on (a) the patient's responses to the signals (i.e., the therapeutic efficacy of the signals) and (b) the expected energy consumption associated with the signals. The manner in which these two characteristics are weighted can vary from one patient to another. For example, some patients may value high efficacy (e.g., highly effective pain relief) more than low power consumption. Such patients will accordingly be willing to recharge their implanted devices more frequently in order to obtain better pain relief. Other patients, on the other hand, may be willing to tolerate an increase (e.g., a slight increase) in pain in order to reduce the frequency with which they recharge their implanted devices. Process portion 207 can include accounting for (e.g., weighting) patient-specific preferences in order to identify one or more therapy signals or sets of therapy signal delivery parameters that satisfy the patient's requirements.

Figure 3:
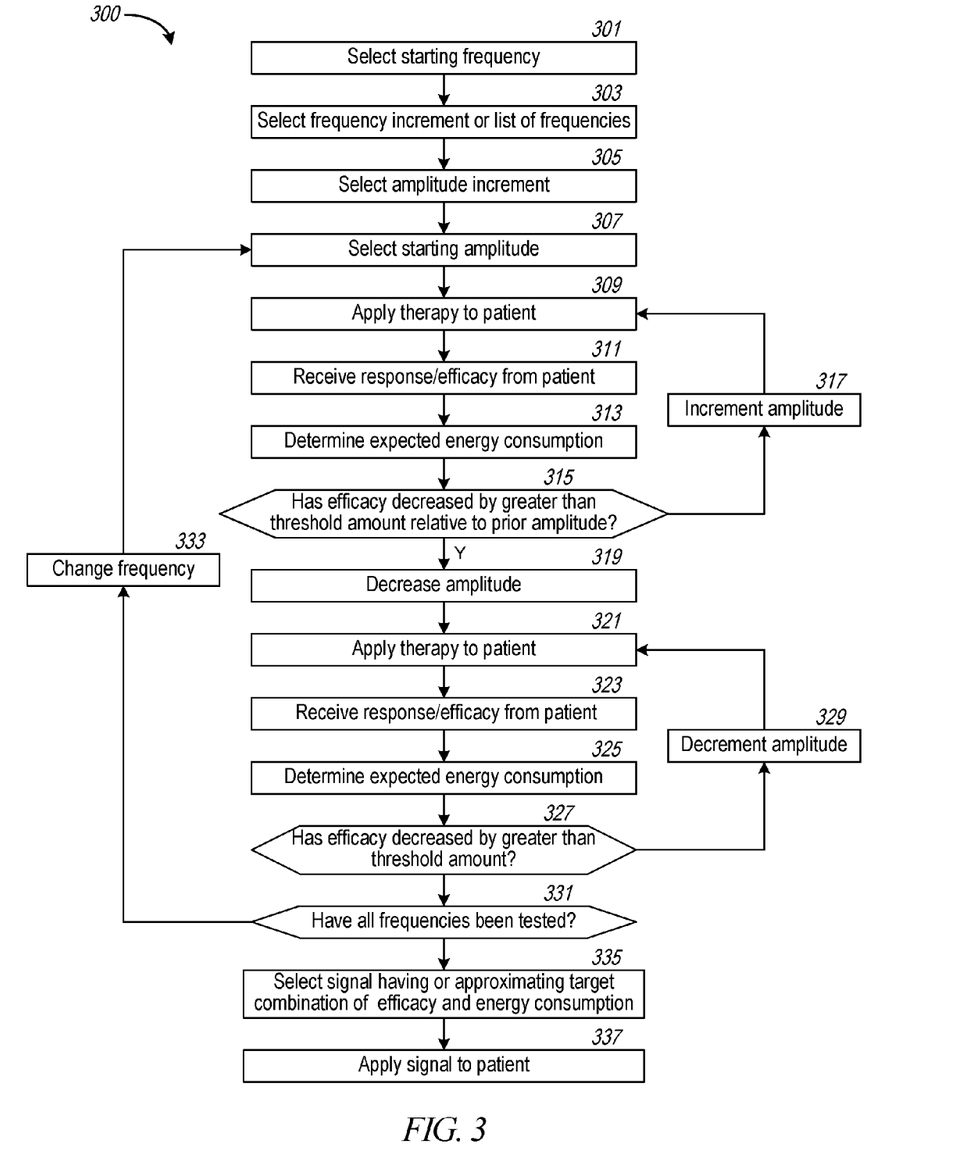
FIG. 3 is a flow diagram illustrating a representative process for selecting signal delivery parameters in accordance with another embodiment of the present technology.

FIG. 3 is a detailed flow diagram illustrating a representative process 300 for selecting signal delivery parameters in accordance with another embodiment of the present technology. In a particular aspect of the illustrated embodiment, it is assumed or determined that other stimulation parameters (such as pulse width and the locations of active contacts, but excluding amplitude) are fixed, e.g., because they provide reasonable efficacy for the patient. The process 300 can include selecting a starting frequency (process portion 301), and selecting a frequency increment or list of frequencies (process portion 303). For example, process portion 301 can include selecting 10 kHz as a starting frequency and process portion 303 can include selecting a list of frequencies that includes 10 kHz and 1.5 kHz. In this simple example, just these two frequencies will be tested, at a variety of signal delivery amplitudes. In other cases, the list of frequencies can include more values (e.g., 10 kHz, 5 kHz, and 1.5 kHz). In still further embodiments, a frequency increment can be used, e.g., in lieu of a list of frequencies. For example, the frequency increment can be 1 kHz, so that multiple frequencies, spaced apart from each other by the 1 kHz increment, can be tested over the course of the process. Accordingly, the process can allow the practitioner, manufacturer, and/or other professional to select the number of frequencies tested, the values of the frequencies, and the manner in which the frequencies are selected in different ways for different patients.

In process portion 305, the process 300 includes selecting an amplitude increment. The amplitude increment can be selected to allow the process to cover a suitably wide range of amplitudes within a reasonable period of time. It has been observed that the efficacy of particular high frequency therapy signals may take some time to develop. This is unlike the case for standard, low frequency SCS treatments, during which the patient can immediately identify whether or not the paresthesia associated with a particular therapy signal masks or overlies the pain. Instead, the effects of high frequency signals, or changes in high frequency signals, may take several hours to a day or so for the patient to detect. Accordingly, the amplitude increment can be selected by the practitioner to allow a reasonable number of different amplitudes to be tested over a reasonable period of time. For example, the practitioner can set the increment to be 0.1 mA in a particular embodiment so as to cover five different amplitudes over a period of five days, assuming the amplitude is incremented once every day. In other embodiments, the practitioner can select other suitable values, e.g., ranging from about 0.1 mA to about 2 mA, and ranging from about 0.5 days to about 5 days, with a representative value of from 1-2 days.

At process portion 307, the starting amplitude is selected. The starting amplitude will typically be selected to be at a value that produces effective therapy. In process portion 309, the therapy is applied to the patient at the starting frequency and starting amplitude. Process portion 311 includes receiving a response or efficacy measure from the patient. The response can include the patient providing a pain score in accordance with any of the scales or measures described above. The patient can provide this pain score via the patient remote 106 (FIG. 1A) so that the value is automatically stored, e.g., at the patient remote, or at the patient's implanted pulse generator. Process portion 313 includes determining the expected energy consumption associated with the combination of frequency and amplitude applied to the patient. This process can be executed by the patient remote 106 or other patient-controllable device, or by the implanted pulse generator (IPG) 101, or by another device. In particular embodiments, the process of determining the expected energy consumption need not be conducted in the sequence shown in FIG. 3. Instead, it can be conducted after or before all the planned combinations of amplitude and frequency have been tested. In particular, a more accurate estimate of the energy consumption may include the actual time the patient uses each frequency and amplitude pair. In any of these embodiments, the energy consumption can be expressed in a variety of suitable manners, including energy per unit time (e.g., power).

Process portion 315 includes determining whether the efficacy, as indicated by the patient, has decreased by greater than a threshold amount relative to the baseline efficacy present at process portion 301. The threshold amount can be selected by the patient and/or practitioner. For example, the threshold can be selected to be a 10%, 20%, 30%, 40% or other decrease from an initial or baseline efficacy value. If this is the first tested amplitude at the selected frequency, this step can be skipped. If not, and it is determined that the efficacy has not decreased by greater than a threshold amount, then the amplitude is incremented, as indicated at process portion 317, and the steps of applying the therapy to the patient, receiving the patient's response and determining the expected energy consumption are repeated. If the efficacy has decreased by greater than the threshold amount, then the process moves to process portion 319. Accordingly, the range within which the amplitude is increased is controlled by the threshold value. This range can also be governed or controlled by other limits. For example, the IPG can have manufacturer-set or practitioner-set limits on the amount by which the amplitude can be changed, and these limits can override amplitude values that might be within the efficacy thresholds described above. In addition, the patient can always override any active program by decreasing the amplitude or shutting the IPG down, via the patient remote 106 (FIG. 1A).

After it has been determined that the efficacy has decreased by at least the threshold amount, the amplitude is decreased at process portion 319. In a particular embodiment, the amplitude can be decreased back to the starting amplitude set in process portion 307, and the amplitude tests (with decreasing amplitude) can continue from that point. In another embodiment, if it is desired to re-test amplitudes that have already been tested in process portions 309-315, those amplitudes can be re-tested as the amplitude is decremented from the value that resulted in the efficacy threshold being met or exceeded.

In process 321, the therapy is applied to the patient at the decreased amplitude and the process of testing the therapeutic efficacy at multiple amplitudes is reiterated in a manner generally similar to that described above with reference to incrementing the amplitude. In particular, process portions 323 (receiving a response and/or efficacy measure from the patient), and process portion 325 (determining the expected energy consumption associated with the decreased amplitude) are repeated as the amplitude is decreased. In process portion 327, the process includes determining whether the efficacy has decreased by greater than a threshold amount. This threshold amount can be the same as or different than the threshold amount used in process portion 315. If it has not decreased by more than the threshold amount, the loop of decreasing amplitude (process portion 329), applying the signal to the patient, and testing the result is repeated until it does.

In process portion 331, the process includes determining whether all frequencies to be tested have in fact been tested. If not, in process portion 333, the frequency is changed and the process of incrementing and then decrementing the amplitude is repeated at the new frequency. If all frequencies have been tested, then process 335 includes selecting the signal or signals having or approximating a target combination of efficacy and energy consumption.

In a simple case, for example, if the practitioner tests 10 kHz and 1.5 kHz at a variety of amplitudes, process portion 335 can also be fairly simple. For example, process portion 335 can include determining if the lowest amplitude that produces effective therapy at 10 kHz also produces effective therapy at 1.5 kHz. If it does, then clearly the energy consumption at 1.5 kHz will be less than the energy consumption at 10 kHz, at the same amplitude. Accordingly, process portion 335 can include selecting the frequency to be 1.5 kHz for delivering additional signals to the patient. Furthermore, if it is clear that all tested amplitudes at 1.5 kHz will consume less energy than even the lowest amplitude at 10 kHz, then process portion 335 can include determining whether any of the amplitudes at 1.5 kHz produce effective pain relief. If any do, the process can include selecting the lowest amplitude that does so.

In other embodiments, process portion 335 can include a more involved process of pairing pain scores and energy consumption levels for each of the tested combinations and automatically or manually selecting the pair that produces the expected best efficacy at the expected lowest energy consumption. The energy consumption can be calculated, expressed, and/or otherwise described as a total amount of energy over a period of time, an energy rate (power) and/or other suitable values. The selection process will include weighting pain reduction and energy consumption in accordance with any preferences, e.g., patient-specific preferences. Accordingly, the patient may prefer a less-than-optimum pain score, but improved power consumption, or vice versa. In any of these embodiments, the selected signal is then applied to the patient in process portion 337, e.g., to provide a course of therapy. The foregoing process can be repeated if desired, for example, if the patient's condition changes over the course of time.

One feature of the foregoing embodiments is that the manufacturer or practitioner can select the range of amplitudes over which the foregoing tests are conducted to be well higher than the point at which therapeutic efficacy is expected to decrease significantly, yet below the point at which the patient is expected to experience any uncomfortable or undesirable side effects. For example, in a particular embodiment, the patient is expected to receive effective therapeutic results at an amplitude range of from about 2 mA to about 6 mA. The overall amplitude test range can be selected to be between about 0 mA and about 10 mA or another suitable value that is not expected to produce undesirable side effects. As a result, the system can automatically test a suitable number of amplitude values and frequency values, without placing the patient in any discomfort. As a further result, the system can automatically test the foregoing amplitude and frequency values in an autonomous manner, without requiring practitioner or patient action, beyond the patient recording pain scores or other responses as the parameters change. Accordingly, the process for identifying an effective, low power consumption therapy signal can be more fully automated than existing processes and can accordingly be easier, less time-consuming, and/or less expensive to perform.

From the foregoing, it will be appreciated that specific embodiments of the presently-disclosed technology have been described herein for purposes of illustration, but that various modifications may be made without deviating from the disclosed technology. For example, several embodiments were described above in the context of variations in the amplitude and frequency of the signal, in order to determine an effective yet low-power therapy signal. In other embodiments, the process can include other parameters that are also varied to determine low-power effective therapy signals, in combination with amplitude and frequency, or in lieu of amplitude and frequency. Suitable signal parameters include pulse width, inter-pulse interval, and duty cycle.

Other embodiments of the present technology can include further variations. For example, instead of selecting an amplitude increment, as discussed above with reference to FIG. 3, a list of amplitude values can be used to increment and/or decrement from a starting amplitude value. The patient can receive a prompt (e.g., via the patient remote) when the system requires an input, such as a pain score. Instead of varying the amplitude at a constant frequency, the system can vary the frequency at a constant amplitude. Instead of first increasing amplitude and then decreasing amplitude, these processes can be reversed. In another embodiment the amplitude can be changed in only one direction, e.g., by starting at zero amplitude or starting at the top of the amplitude test range.

As discussed above, many of the steps for carrying out the foregoing processes are performed automatically, without continual involvement by the patient and/or practitioner. The instructions for carrying out these steps may be carried on any suitable computer-readable medium or media, and the medium or media may be distributed over one or more components. For example, certain steps may be carried out by instructions carried by the IPG, the patient remote and/or the physician's programmer, depending on the embodiment. Accordingly, a portion of the instructions may be carried by one device (e.g., instructions for receiving patient responses may be carried by the patient remote), and another portion of the instructions may be carried by another device (e.g., the instructions for incrementing and decrementing the amplitude may be carried by the IPG).

Certain aspects of the technology described in the context of particular embodiments may be combined or eliminated in other embodiments. For example, in some embodiments, the foregoing process can include only incrementing the amplitude or only decrementing the amplitude, rather than both, as discussed above. In other embodiments, certain steps of the overall process can be re-ordered. For example, the expected energy consumption value can be determined before or after receiving a response from the patient, and/or can be performed on a list of amplitude values all at one time. In some embodiments, certain amplitude/response pairs may be eliminated from consideration or from further calculations, e.g., if the data are determined to be defective, and/or for any other suitable reason.

3.0 Additional Embodiments

In one embodiment, there is provided a method for programming a spinal cord stimulation system for providing pain relief to a patient. The method comprises configuring a signal generator to deliver a first therapy signal at a first frequency, and a second therapy signal at a second frequency different than the first. For both the first and second signals, the method includes carrying out the following processes: (i) increasing an amplitude of the signal, over multiple steps, from a baseline amplitude at which the patient has a baseline response; (ii) for individual step increases, determining the patient's response to the increased amplitude; (iii) decreasing the amplitude over multiple steps; and (iv) for individual step decreases, determining the patient's response to the decreased amplitude. The method can further include comparing the patient responses to the first therapy signal with the patient responses to the second therapy signal and, based on the patient responses and an expected energy consumption for the first and second therapy signals, selecting one of the first and second therapy signals for additional therapy to the patient.

In particular embodiments, the first frequency can be in a frequency range from 10 kHz to 100 kHz, inclusive, and the second frequency can be in a frequency range from 1.5 kHz to 10 kHz. The process of increasing or decreasing the amplitude can be halted if the pain score worsens by a threshold value, and the threshold value can vary from 10% to 40%, in particular embodiments.

Another representative embodiment of the technology is directed to a spinal cord stimulation system. The system comprises a signal generator coupleable to a signal delivery device to deliver electrical therapy signals to a patient at a first frequency and a second frequency different than the first. The system can further include a computer-readable medium programmed with instructions that, when executed, for both the first and second signals: (i) increases an amplitude of the signal, over multiple steps, from a baseline amplitude at which the patient has a baseline response; (ii) at individual step increases, receives the pain score based on the patient's response to the increased amplitude; (iii) decreases the amplitude over multiple steps; and (iv) for individual step decreases, receives the pain score based on the patient's response to the decreased amplitude. The instructions compare the pain scores corresponding to the first therapy signal with the pain scores corresponding to the second therapy signal. Based on the pain scores and an expected energy consumption for each of the first and second therapy signals, the instructions determine one of the first and second therapy signals for additional therapy to the patient.

I claim:

1. A method for configuring a spinal cord stimulation system for providing pain relief to a patient, wherein the spinal cord stimulation system includes a signal generator configured to generate an electrical therapy signal, and a signal delivery device configured to receive the electrical therapy signal from the signal generator and deliver the electrical therapy signal to the patient's spinal cord region, the method comprising:
(a) configuring the signal generator to deliver a first therapy signal with a first set of therapy signal parameters, wherein the first set of therapy signal parameters includes a first frequency in a frequency range from 10 kHz to 100 kHz, inclusive;
(b) configuring the signal generator to deliver a second therapy signal with a second set of therapy signal parameters, wherein the second set of therapy signal parameters includes a second frequency in a frequency range from 1.5 kHz to 10 kHz,
(c) for both the first and second signals:
  (i) increasing an amplitude of the signal, over multiple steps, from a baseline amplitude at which the patient has a baseline pain score;
  (ii) for individual step increases, determining a pain score based on the patient's response to the increased amplitude;
  (iii) decreasing the amplitude over multiple steps; and
  (iv) for individual step decreases, determining a pain score based on the patient's response to the decreased amplitude;
(d) comparing the pain scores corresponding to the first therapy signal with the pain scores corresponding to the second therapy signal; and
(e) based on the pain scores and an expected energy consumption for the first and second therapy signals, selecting one of the first and second therapy signals for additional therapy to the patient.

2. The method of claim 1, further comprising halting at least one of increasing or decreasing the amplitude if the pain score worsens by at least a threshold value.

3. The method of claim 2 wherein the threshold value is from 10% to 40%, inclusive, of the patient's baseline pain score.

4. The method of claim 2 wherein the threshold value is from 15% to 35%, inclusive, of the patient's baseline pain score.

5. The method of claim 2 wherein the threshold value is from 10% to 20%, inclusive, of the patient's baseline pain score.

6. The method of claim 2 wherein the threshold value is selected by the patient.

7. The method of claim 1 wherein selecting one of the first and second signals includes selecting the second signal if a pain score corresponding to the second signal at a particular amplitude is the same as or better than a pain score corresponding to the first signal at the same particular amplitude.

8. The method of claim 1 wherein the pain score is selected from the group comprising a VAS, NRS, or Likert score.

9. A method for programming a spinal cord stimulation system for providing pain relief to a patient, the method comprising:
(a) configuring a signal generator to deliver a first therapy signal at a first frequency;
(b) configuring the signal generator to deliver a second therapy signal at a second frequency different than the first,
(c) for both the first and second signals:
  (i) increasing an amplitude of the signal, over multiple steps, from a baseline amplitude at which the patient has a baseline response;
  (ii) for individual step increases, determining the patient's response to the increased amplitude;
  (iii) decreasing the amplitude over multiple steps; and
  (iv) for individual step decreases, determining the patient's response to the decreased amplitude;
(d) comparing the patient responses to the first therapy signal with the patient responses to the second therapy signal, wherein the patient responses include at least one of a pain score or a value correlated with the patient's pain level; and
(e) based on the patient responses and an expected energy consumption for the first and second therapy signals, selecting one of the first and second therapy signals for additional therapy to the patient.

10. The method of claim 9 wherein the second frequency is lower than the first frequency.

11. The method of claim 10 wherein, if a patient response to the second signal at a particular amplitude is the same as or better than a patient response to the first signal at the same particular amplitude, selecting one of the first and second therapy signals includes selecting the second therapy signal.

12. The method of claim 9 wherein selecting includes selecting a combination of amplitude and frequency that produces a less than optimum pain score to obtain lower energy consumption.

13. The method of claim 9 wherein selecting includes selecting a combination of amplitude and frequency that produces less than optimum energy consumption to obtain a lower pain score.

14. The method of claim 9 wherein selecting includes selecting a combination of amplitude and frequency that produces the lowest energy consumption and lowest pain score obtained as a result of increasing and decreasing the amplitude at the first and second frequencies.

15. A spinal cord stimulation system, comprising:
a signal generator coupleable to a signal delivery device to deliver electrical therapy signals to a patient at a first frequency and a second frequency different than the first; and
a non-transitory computer readable medium programmed with instructions that, when executed:
for both the first and second signals,
  (i) increase an amplitude of the signal, over multiple steps, from a baseline amplitude at which the patient has a baseline response;
  (ii) at individual step increases, receive a pain score based on the patient's response to the increased amplitude;
  (iii) decrease the amplitude over multiple steps; and
  (iv) for individual step decreases, receive a pain score based on the patient's response to the decreased amplitude;
compare the pain scores corresponding to the first therapy signal to the pain scores corresponding to the second therapy signal; and
based on the pain scores and an expected energy consumption for each of the first and second therapy signals, select one of the first and second therapy signals for additional therapy to the patient.

16. The system of claim 15 wherein the signal generator is an implantable signal generator.

17. The system of claim 16 wherein the computer-readable medium is carried by the implantable signal generator.

18. The system of claim 16 wherein a first portion of the computer-readable medium is carried by the implantable signal generator and a second portion of the computer-readable medium is carried off the implantable signal generator.

19. The system of claim 16 wherein a first portion of the instructions are executed by the implantable signal generator and a second portion of the instructions are carried out by a patient remote.

20. The system of claim 15 wherein an incremental value for increasing and decreasing the amplitude is 0.1 mA.

21. The system of claim 15 wherein the first frequency is higher than the second frequency.

22. The system of claim 15 wherein the first and second frequencies are both at least 1.5 kHz.

23. The system of claim 15 wherein the first frequency is from 10 kHz to 100 kHz, inclusive and the second frequency is from 1.5 kHz to 10 kHz.

* * * * *